(12) United States Patent
Bond et al.

(10) Patent No.: US 8,582,837 B2
(45) Date of Patent: Nov. 12, 2013

(54) PSEUDO-TRANSLUCENT INTEGRATED CIRCUIT PACKAGE

(75) Inventors: Robert Henry Bond, Oakland, CA (US); Alan Kramer, Berkeley, CA (US); Giovanni Gozzini, Berkeley, CA (US)

(73) Assignee: Authentec, Inc., Melbourne, FL (US)

( * ) Notice: Subject to any disclaimer, the term of this patent is extended or adjusted under 35 U.S.C. 154(b) by 963 days.

(21) Appl. No.: 12/355,673

(22) Filed: Jan. 16, 2009

(65) Prior Publication Data

US 2009/0169071 A1 Jul. 2, 2009

Related U.S. Application Data

(63) Continuation-in-part of application No. 11/967,883, filed on Dec. 31, 2007.

(51) Int. Cl.
*G06K 9/00* (2006.01)
(52) U.S. Cl.
USPC ............ 382/124; 382/115; 382/116; 382/141
(58) Field of Classification Search
USPC ................... 382/124, 141, 115–116; 257/98, 257/E33.059
See application file for complete search history.

(56) References Cited

U.S. PATENT DOCUMENTS

| | | | |
|---|---|---|---|
| 5,844,287 A | 12/1998 | Hassan et al. | |
| 5,864,296 A | 1/1999 | Upton | |
| 5,942,761 A | 8/1999 | Tuli | |
| 5,963,679 A | 10/1999 | Setlak | |
| 6,061,464 A | 5/2000 | Leger | |
| 6,980,286 B1 | 12/2005 | Feng | |
| 7,147,153 B2 | 12/2006 | Rowe et al. | |
| 2003/0103686 A1 | 6/2003 | Ogura | |
| 2005/0069181 A1 | 3/2005 | Setlak | |
| 2006/0063015 A1 | 3/2006 | McCormick | |
| 2006/0181521 A1 | 8/2006 | Perreault | |
| 2007/0122013 A1 | 5/2007 | Setlak | |

FOREIGN PATENT DOCUMENTS

| | | |
|---|---|---|
| EP | 1 816 587 | 8/2007 |
| EP | 10150187 | 6/2010 |
| WO | 2006041780 | 4/2006 |

OTHER PUBLICATIONS

Rowe, Robert K., "A Multispectral Sensor for Fingerprint Spoof Detection", Sensors, vol. 22, No. 1, (Jan. 2005), pp. 2-4.
http://www.validityinc.com/post.aspx?id=147, "Validity Launches the First Customizable LED Fingerprint Sensor", Jan. 8, 2009.
"VFS301 Fingerprint Sensor Product Brief", www.validityinc.com/news/wp-content/uploads/2009/01/vfs301-fingerprint-sensor-product-brief.pdf, Jan. 2, 2009.

*Primary Examiner* — Ruiping Li
(74) *Attorney, Agent, or Firm* — Allen, Dyer, Doppelt, Milbrath & Gilchrist, P.A.

(57) ABSTRACT

An integrated circuit (IC) package includes at least one light source disposed together with an IC structure within an encapsulation structure. The material forming the encapsulation structure is generally opaque. Accordingly, the light source and at least a portion of the IC are not visible to the unaided human eye. The thickness and geometry of the encapsulation are such that when the light source is caused to emit light, the encapsulation structure permits at least a portion of that light to be visible to a user. The IC may be a portion of a fingerprint sensor, exposed for receiving a fingertip of a user. The light source, or a plurality of such light sources, may be functional (e.g., providing visual indication of the of the condition or state of an item of hardware or software, assist the user in operation of a device), be primarily aesthetic, or a combination thereof.

22 Claims, 8 Drawing Sheets

PSEUDO-TRANSLUCENT INTEGRATED CIRCUIT PACKAGE

CROSS-REFERENCE TO RELATED APPLICATIONS

The present application is a continuation-in-part of copending U.S. application for Letters Patent titled "Hybrid Multi-Sensor Biometric Identification Device" Ser. No. 11/967,883, filed on Dec. 31, 2007, which, in its entirety, is hereby incorporated herein by reference and to which priority is claimed.

BACKGROUND

The present disclosure is related to integrated circuit packaging, and more particularly to an integrated circuit package which includes a light source such as a light emitting diode or the like together with an integrated circuit which are encapsulated in an opaque encapsulation material such that when the light source emits light, at least some of that light may be seen on the surface of the opaque encapsulation material.

Associating a light source with a semiconductor device is known in the art. The light source may serve a purely functional role, such as in an optical fingerprint sensor, which uses the light source to illuminate a portion of a finger. In one example, the illuminated portion of the finger is then examined and a fingerprint pattern captured therefrom. See U.S. Pat. No. 7,440,597, incorporated herein by reference.

Light sources associated with semiconductor packages may also have other uses, such as providing a user with some sort of visual feedback during operation of a device. See, for example, www.validityinc.com/post.aspx?id=147. Another example is disclosed in U.S. Pat. No. 7,272,723, incorporated herein by reference, in which a light emitting diode (LED) provides a user with a visual indication of the operations being performed by a peripheral key management device. In one embodiment of such a device, the light source is in electrical communication with a substrate which has electrical connection to processing hardware. The light source and substrate are enclosed within the interior of a partially translucent or transparent housing. As is typical for such devices, the housing is a structure molded prior to introducing the substrate and LED. During assembly of the final device, the substrate and LED are secured within the pre-molded housing. In general, such devices are relatively large, and while electrically coupled to the substrate, the light source is not mounted on or an integral part thereof.

In general, there is great pressure on producers of integrated circuit-based device to provide ever-more compact devices with a lower cost of manufacture. Silicon-based sensors, such as capacitive fingerprint sensors, are one such example. These silicon fingerprint sensing devices are commonly found in laptop computers, in PC peripherals such as keyboards and mice, in some models of cell phones and personal digital assistance devices (PDAs) and so forth. The small amount of space available for these devices mandates as much integration of the components comprising the silicon fingerprint sensor as possible. And the supply chain model puts great pressure on device suppliers to lower costs.

Yet, there is also great pressure to innovate and introduce new features to provide product differentiation, ease of use, reliability and so on. One such feature in the area of silicon fingerprint sensors is an attractive device appearance. Another is a visual mechanism for providing a user with feedback on device status and operation, such as where and when to swipe or place a finger over a sensor, whether a swipe or finger placement was successful, and so forth.

To date, there has not been available an IC package design which provides an attractive appearance, visual user feedback, and other functionality of an illuminated integrated circuit package (again, of which a capacitive fingerprint sensor is one example), while also being of compact footprint, compatible with existing manufacturing techniques, materials, and tools, and which does not otherwise increase the cost of device manufacturing more than the cost of the light source itself. The present invention addresses these shortfalls.

SUMMARY

The present disclosure is directed to an integrated circuit (IC) package which includes at least one light source such as a light emitting diode (LED) disposed therewith within an opaque encapsulation structure. The material forming the encapsulation structure is of a type known in the art. The thickness and geometry of the encapsulation is such that when the light source is caused to emit light, the encapsulation material permits at least a portion of that light to be emitted, yet the unaided eye (i.e., without equipment employed to view into an opaque structure or to view at a high level of magnification) is not able to see the physical structure of the light source within the encapsulation structure.

According to one aspect of the invention disclosed herein, the IC package includes a package base, an LED secured to the package base, an IC also secured to the package base, electrical interconnections between the LED and the IC, and encapsulation material encapsulating the IC package base, the LED, the IC, and the connections between the LED and IC. In another embodiment, the LED is integrally formed within and forms a part of the IC, which together are disposed with the encapsulation material.

According to another aspect of the invention disclosed herein, the IC package includes a package base, at least one LED secured to the package base, a silicon biometric sensor IC (including a sensor and related circuitry) also secured to the package base, and connections carried by the package base such that the LED(S) may be electrically controlled directly by the sensor IC circuitry or by other indirect or external circuitry. In a variation of this aspect of the invention, the biometric sensor is a capacitive fingerprint sensor, and the encapsulation material is formed such that a portion of the sensor IC surface is left minimally encapsulated or free of encapsulation material (i.e., an exposed sensor portion is formed in the encapsulation structure. In still another variation, the encapsulation structure is formed to have at least two opposingly disposed sidewalls at the periphery of the exposed sensor portion of a thickness and geometry such that a portion of the light emitted by the light source is caused to be visible on the surface of the exposed sensor at least through a region of those sidewalls.

In each exemplary embodiment of the present invention, a conventional encapsulation material is used. Such traditional encapsulation materials are typically considered opaque to the unaided human eye. However, thicknesses and geometries of the encapsulation structure are chosen such that when the light source is caused to emit light, the encapsulation structure permits diffused light from the light source to be visible on the surface of the encapsulation structure such that the encapsulation material appears translucent, and making visible to the human eye the light and the color of the light emitted by the light source. When the light source is not emitting light, the encapsulation material retains its traditional opaque appearance, and the user is not able to see the light source (or any other components) encapsulated therein.

In certain exemplary embodiments, a single light source is disposed within the encapsulation structure. In other exemplary embodiments, multiple light sources are disposed within the encapsulation structure. In the case of multiple light sources, such light sources may each be of the same color, or two or more of the light sources may be of different colors. Furthermore, in certain embodiments the light source is an LED, while in other embodiments the light source is an alternate device type, such as an organic light emitting device (OLED), a low-power solid-state laser, etc.

The light source so disposed can be used in a variety of applications to convey to a user the condition of a device or other hardware or software (e.g., active of inactive), state condition of a device or other hardware or software (e.g., ready for input or currently processing input), visual cues as to expected or requested user action (e.g., a request for a user to push a button or swipe a finger over a sensor), visual cues as to location of a portion of hardware to be activated or utilized (e.g., which button to push or where and when to slide a finger), visual feedback regarding the status of performance of steps of a process and so forth. Different colors may be used to supplement or enhance the information (e.g., green light emitted for a successful fingerprint scan and yellow light emitted for a failed fingerprint scan). It allows a human user to be provided with information about a function(s) or apparatus based on lighting conditions such as "on"-"off", blinking, dimming/brightening, unique sequence of flashes, colors, etc. Furthermore, the light emitted by the light source may be purely aesthetic, or a combination of aesthetic and functional.

By embedding the light source in the encapsulating material, the light source is environmentally protected from harsh or corrosive conditions and materials. Embedding the light source in the encapsulating material such that light therefrom is visible only when it is illuminated results in a simpler, cleaner appearance which is more attractive to a user. By employing traditional opaque encapsulating materials as opposed to special transparent materials, special material and special equipment costs are eliminated, processing time is reduced, yield losses are reduced, and processing complexity is reduced.

The above is a summary of a number of the unique aspects, features, and advantages of the present disclosure. However, this summary is not exhaustive. Thus, these and other aspects, features, and advantages of the present disclosure will become more apparent from the following detailed description and the appended drawings, when considered in light of the claims provided herein.

BRIEF DESCRIPTION OF THE DRAWINGS

In the drawings appended hereto like reference numerals denote like elements between the various drawings. While illustrative, the drawings are not drawn to scale. In the drawings.

DETAILED DESCRIPTION

Figure 1:
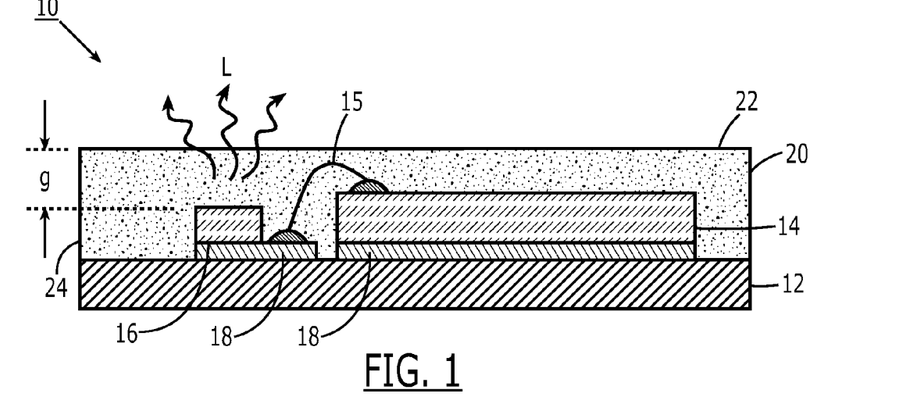
FIG. 1 is a cut-away cross-sectional view of an integrated circuit (IC) package with integrally encapsulated light source where the light source is directly controlled by the integrated circuit according to an embodiment of the present invention.

With reference to FIG. 1, there is shown therein a cross-sectional view of an integrated circuit (IC) package 10 according to a first embodiment of the present invention. IC package 10 comprises an IC package base 12, having attached thereto, or alternatively having formed thereon, an IC 14 (one such IC being shown, and it being understood that more than one IC may also be included in such an IC package). IC package base 12 may, for example be an insulative fiberglass panel of the type commonly used to form a printed circuit board (PCB). Wire bonds 15 (or other connection not shown) may be employed to make any required electrical interconnections between electrical connections 18 formed on the surface of IC package base 12. In this example, IC package base 12 may be a printed circuit board formed with patterned electrical connections 18 for the specific purpose of receiving IC 14 and light source 16 (and possibly other components.) The scope of the present invention is not intended to be limited by the operations performed by IC 14, although as described further below in certain exemplary embodiments IC 14 may have specific functionality. Thus, in this first embodiment IC 14 may perform virtually any function known or later developed in the art.

Also attached to IC package base 12, or alternatively formed therein, is a light source 16. In the embodiment shown, light source 16 is an otherwise well-known light emitting diode (LED), although the scope of the present invention is not intended to be limited by the structure nor mode of operation of light source 16. For example, light source 16 may be a monochromatic, inorganic (crystalline)-based semiconductor LED (OLED). Light source 16 may be mounted within a housing and optionally may have a dispersion lens integrally formed in the housing. Light source 16 (or the material encasing same) may produce light in one of a variety of colors, or multiple colors, or may optionally include a phosphor diffuser for white light emission. Light source 16 (or the material encasing same) may emit light in specific directions around the periphery of the light source. Light source 16 may also be a solid state, multiple quantum well heterostructure laser. Light source 16 may be a complete, packaged device with interconnections, or may be a bare die (similar to an IC) which is electrically connected to IC 14 by way of wire bonds 15, or by other indirect or external connection shown in FIG. 10 and FIG. 9 respectively.

Encapsulation structure 20 is formed over IC package base 12, IC 14, wire bonds 15, light source 16, and electrical interconnections 18. The material forming encapsulation structure 20 may be a resin or plastic of a type otherwise well known in the art. The encapsulation may be accomplished by die molding or other techniques. A variety of die molding techniques are well known in the art, such as disclosed in U.S. Pat. No. 5,049,526, which is incorporated herein by reference, and thus the application of the encapsulation structure 20 is not further discussed herein.

Importantly, the thickness of the encapsulation structure over and around light source 16 (e.g., the size of gap g between the point of emission of light source 16 and an emission surface, such as top surface 22 of encapsulation structure 20) determines the amount (intensity) of light that may be seen by an unaided human eye through the encapsulation material when light source 16 emits light (e.g., power is provided to light source 16). Emission may be through top surface 22, side surface 24, or other surface as described further below, provided gap g does not exceed a critical thickness to permit emission of light. In fact, as the gap g increases, the intensity of the light visible therethrough decreases. Thus, different light intensities may be obtained by design for different regions of encapsulation structure 20, from a single light source 16, by varying the thickness of the encapsulation material above and around light source 16.

The size of the gap which permits light emission through encapsulation structure 20 will vary depending upon the type and intensity of the light source 16), the type of material forming encapsulation structure 20, the desired level of brightness of the visible light, and so forth. The size of the gap is, however, sufficiently large to hide the physical surfaces of light source 16 (and any other components such as IC 14) within the encapsulation structure. For illustrative purposes, gap g may be on the order of 100 μm (microns). For a gap g of this size, when light source 16 is powered to emit light, a diffuse light can be seen through encapsulation structure 20, and when light source 16 is not powered to emit light, light source 16 cannot be seen within encapsulation structure 20. Light is visible through encapsulation structure 20 when light source 16 is illuminated despite the fact that the encapsulation material is essentially opaque. For this reason, we also refer to encapsulation structure 20 herein as being pseudo-translucent.

Figure 2:
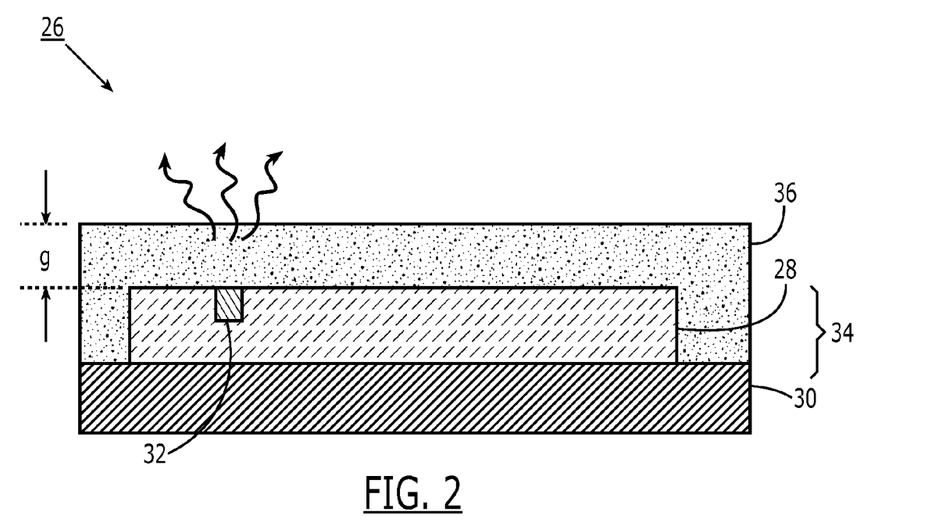
FIG. 2 is a cut-away cross-sectional view of another integrated circuit (IC) package with integrally formed and integrally encapsulated light source according to another embodiment of the present invention.

An alternate embodiment of an IC package 26 is shown in cross-section in FIG. 2. As previously described, IC 14 and light source 16 were separate and discrete elements. According to the embodiment of FIG. 2, an IC 28 is formed to have a light source 32 integrally formed therewith, thereby providing an integrated IC and light source 34. This embodiment contemplates that processing steps forming the active components of IC 28 and processing steps forming light source 32 are either the same or are complementary. Encapsulation structure 36 is then formed over integrated IC and light source 34, as previously described.

Figure 3:
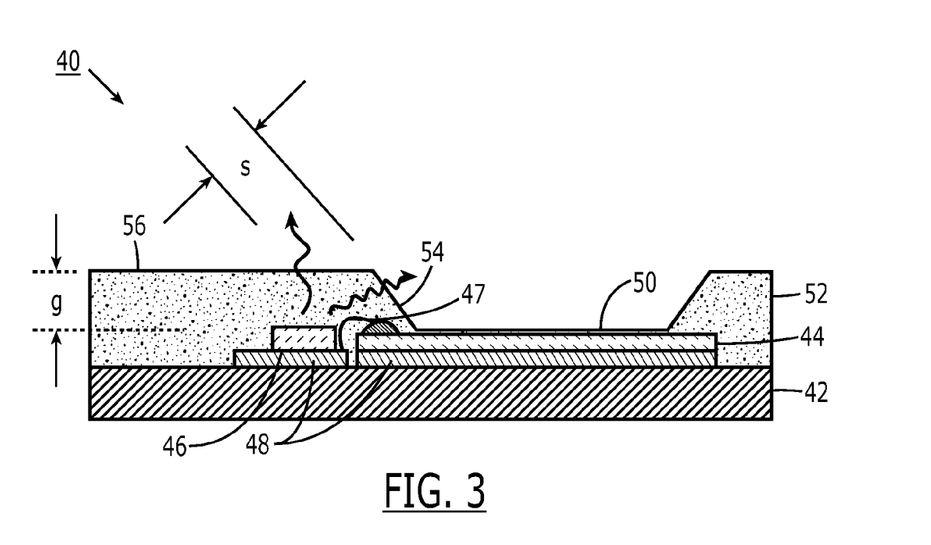
FIG. 3 is a cut-away cross-sectional view of an integrated circuit (IC) package with integrally encapsulated light source and exposed IC surface of a type which may be used in a biometric sensor apparatus according to yet another embodiment of the present invention.

With reference next to FIG. 3, an IC package 40 according to yet another embodiment of the present invention is shown in cross-section. In this embodiment, an IC 44 forms a component of a silicon biometric sensor apparatus, such as a capacitive fingerprint sensor. IC 44 is attached to IC package base 42, and interconnected with light source 46 by wire bond 47 and interconnections 48. As is known, capacitive fingerprint sensors operate with the fingertip of the user located very close to if not in contact with the upper surface 50 of the sensor IC 44. Thus, an encapsulation structure 52 is formed such that a portion of upper surface 50 of IC 44 is exposed or very thinly covered as compared to the encapsulation of the remainder of IC 44, light source 46, wire bond 47, and interconnections 48. This is a so-called "exposed die" encapsulated structure. Many techniques are known for producing an exposed die encapsulated IC, such as that disclosed in U.S. Pat. No. 6,686,227, which is incorporated herein by reference. Thus, the precise method of obtaining the exposed die is not a limitation on the scope of the present invention.

As is typical with the formation of an encapsulated IC with an exposed surface portion, the encapsulation structure 52 defines a number of sidewalls 54 which extend towards the exposed die surface. Typically, there are two such sidewall surfaces, positioned opposite one another on the lateral edges of the exposed die surface. Sidewalls 54 form the channel within which a finger is placed or slid in the process of scanning for a fingerprint pattern or the locators for a finger when a non-scanning biometric sensor is used.

There are a number of applications in which it is desirable to illuminate a portion of or draw attention to a portion of the exposed die surface, such as to indicate to a user where to swipe or position a finger in using the fingerprint sensor. (As the present invention applies equally to strip sensor and area sensor devices, swiping a finger in the case of a strip sensor and placing a finger in the case of an area sensor are collectively referred to herein as presenting a finger.) Therefore, in one embodiment a gap s is formed between the point of emission of light source 46 and the surface of sidewall 54 such that light from light source 46 may be seen by the human eye emitting from sidewall 54. Thickness and geometries may be adjusted such that light preferentially or exclusively emits from sidewall 54, or conversely emits from sidewall 54 with a reduced intensity as compared to top surface 56 of encapsulation structure 52.

Furthermore, light source 46 may be a directional light source, such as a side-emitting LED, positioned such that light therefrom is directed toward sidewall 54 for preferential lighting at the surface of sidewall 54. Light source 46 may also be tilted toward a surface for preferential light output. Yet another way to obtain preferential lighting through sidewall 54 is to apply a coating (not shown) over the topmost surface 56 of encapsulation structure 52 to reduce the amount of light that exits through that surface.

The description above and accompanying figures have thus far illustrated a single light source disposed adjacent the IC within the encapsulation structure. With reference next to the embodiment 58 shown in FIG. 4, it can be seen and appreciated that in any of the foregoing embodiments, an arbitrary number of light sources may be placed virtually anywhere around the periphery of IC 62, such as the placement of light sources 74 and 76 (and light sources 70 and 72 of FIG. 5 discussed further below). Alternatively or in addition, IC 62 can be formed with light sources within its periphery (not shown), so that light may exit the encapsulation structure at virtually any desired location.

Figure 4:
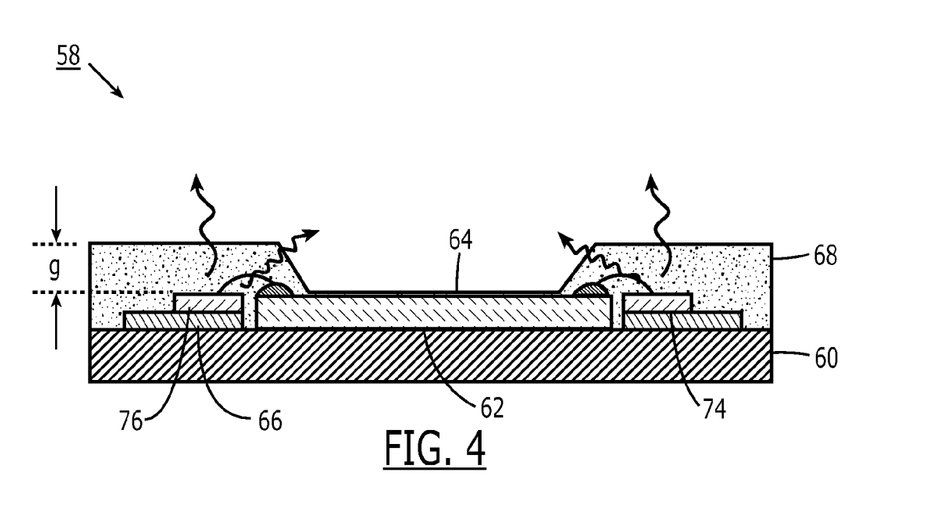
FIG. 4 is a cut-away cross-sectional view of an integrated circuit (IC) package with multiple integrally encapsulated light sources and exposed IC surface of a type which may be used in a biometric sensor apparatus according to still another embodiment of the present invention.
Figure 5:
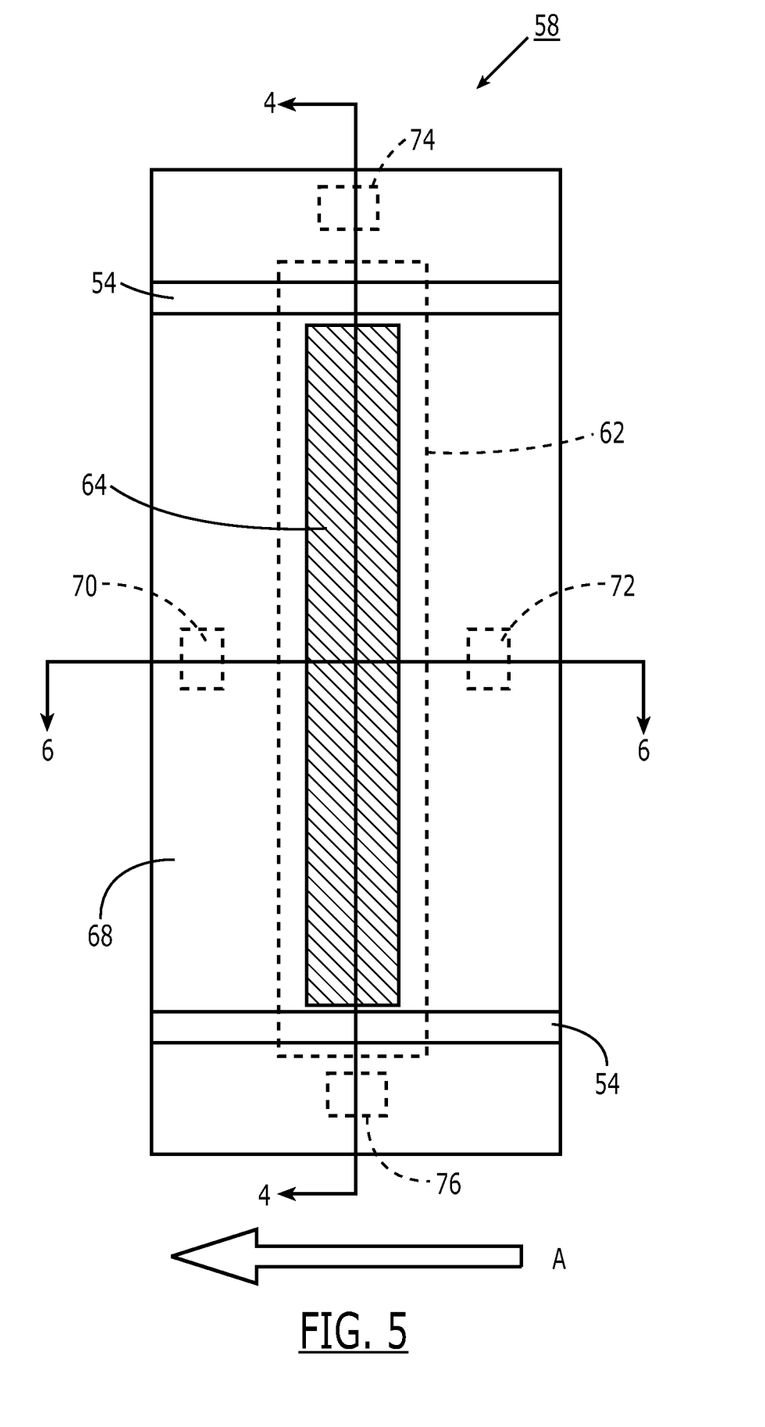
FIG. 5 is a plan view of the integrated circuit (IC) package with multiple integrally encapsulated light sources and exposed IC surface of a type which may be used in a biometric sensor apparatus according to the embodiment illustrated in FIG. 4.

With reference to FIG. 5 which is a top or plan-view of embodiment 58 of the present invention shown in FIG. 4, it can be seen that light sources 70, 72, 74, and 76 have be placed in desired locations around the periphery of IC 62 (which is not visible to the human eye within the encapsulation structure 68, apart from the exposed portion 64 of sensor IC 62). In this embodiment, the structure is used as a silicon fingerprint sensor such as a capacitive fingerprint sensor. As is well known for such devices, a finger is swiped in the direction of arrow A which results in a plurality of image strips being captured for analysis (such as verification against a database of registered fingerprints). Light sources 74 and 76 may be illuminated to provide a visual feedback to a user as to the location of the exposed portion 64 of sensor IC 62 so that the user's finger may be properly aligned. Light sources 70 and 72 may be operated in sequence so that a user is provided with visual feedback as to how to present the finger (e.g., which direction to swipe a finger in the case of a strip sensor). These uses for light sources 70-76 are merely exemplary, and in no way limit the scope of the invention described and claimed here.

Figure 6:
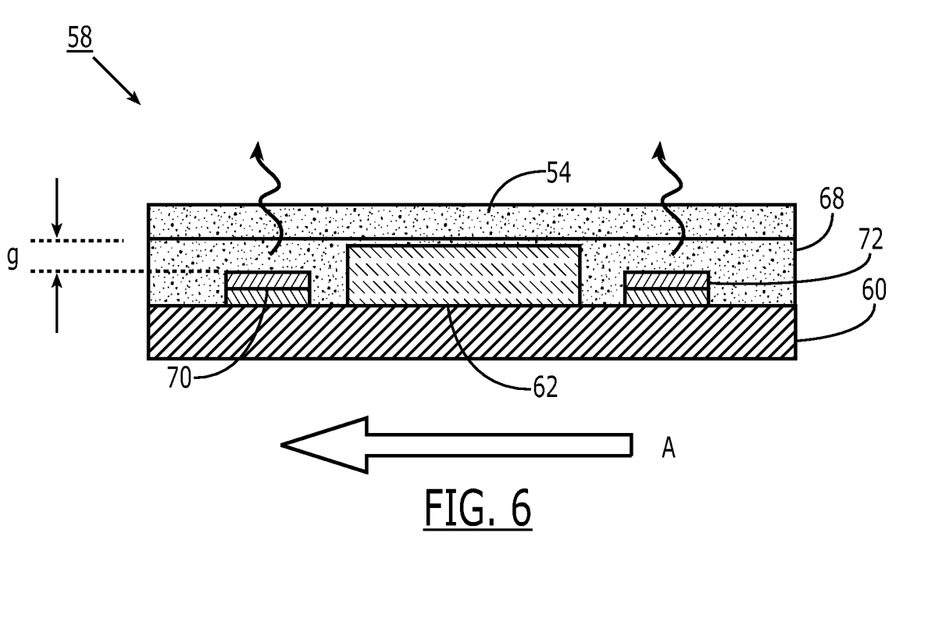
FIG. 6 is a is a cut-away side view of the integrated circuit (IC) package with multiple integrally encapsulated light sources and exposed IC surface of a type which may be used in a biometric sensor apparatus according to the embodiment illustrated in FIGS. 4 and 5, and is a view perpendicular to the view shown in FIG. 4.

FIG. 6 is a cut-away side view of the embodiment 58 shown in FIGS. 4 and 5, and is a view perpendicular to the view shown in FIG. 4. In the view shown in FIG. 6, the position and relationship of light sources 70 and 72 relative to IC 62 can be seen. As previously discussed, the position of the light sources, the number of such light sources, the type and mode of operation of the light sources, the color of light the light sources emit, etc. may be varied depending on the application of the invention disclosed herein. Furthermore, the thickness and geometry (e.g., forming local non-plan regions) of the encapsulation structure 68 encapsulating the light sources may be controlled to obtain a desired light intensity of light to be seen by the human eye at the encapsulation structure surface to be viewed by a user.

Figure 7A:
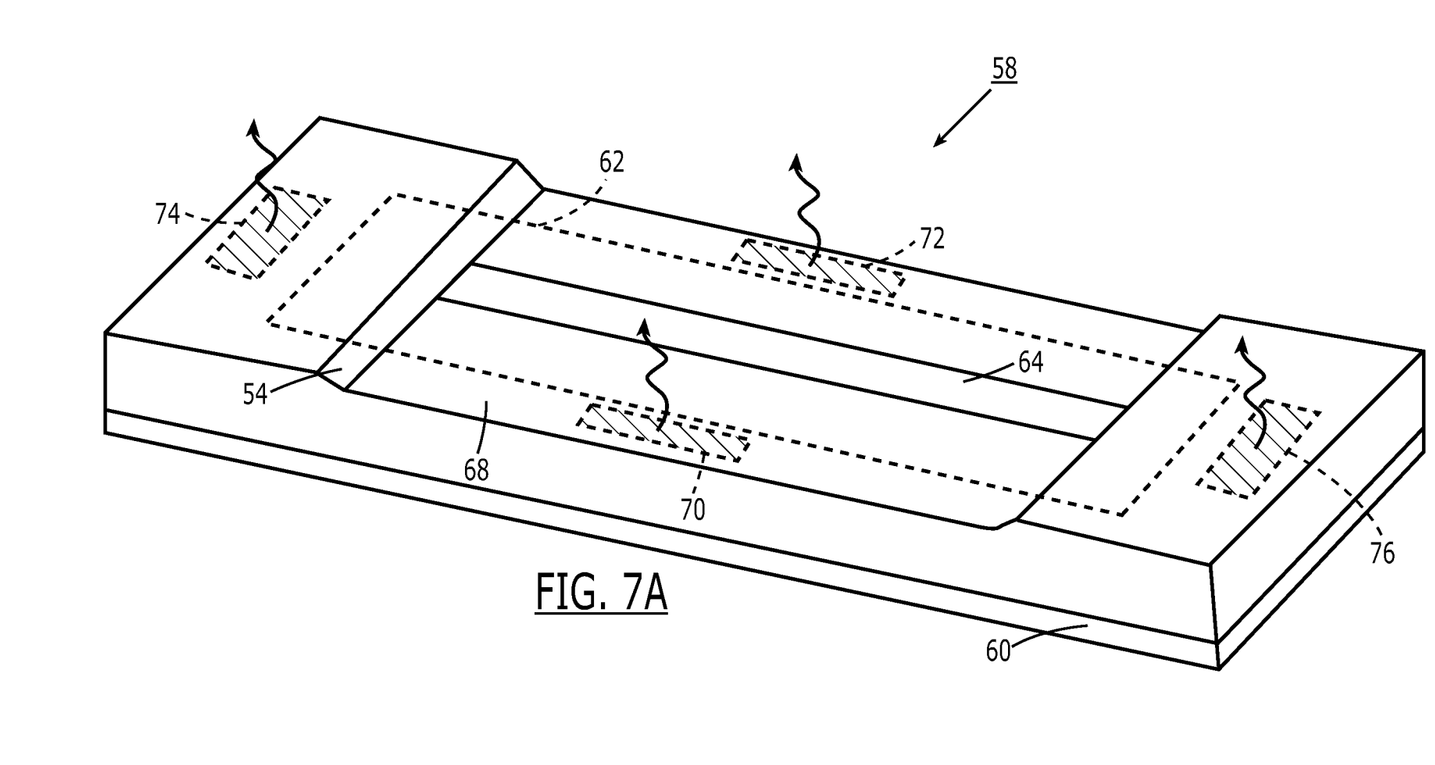
FIG. 7A is a perspective view of the integrated circuit (IC) package with multiple integrally encapsulated illuminated light sources and exposed IC surface of a type which may be used in a biometric sensor apparatus according to the embodiment illustrated in FIGS. 4 and 5, highlighting that light emitted by the light sources (but not the light sources themselves) can be seen through the encapsulation structure.
Figure 7B:
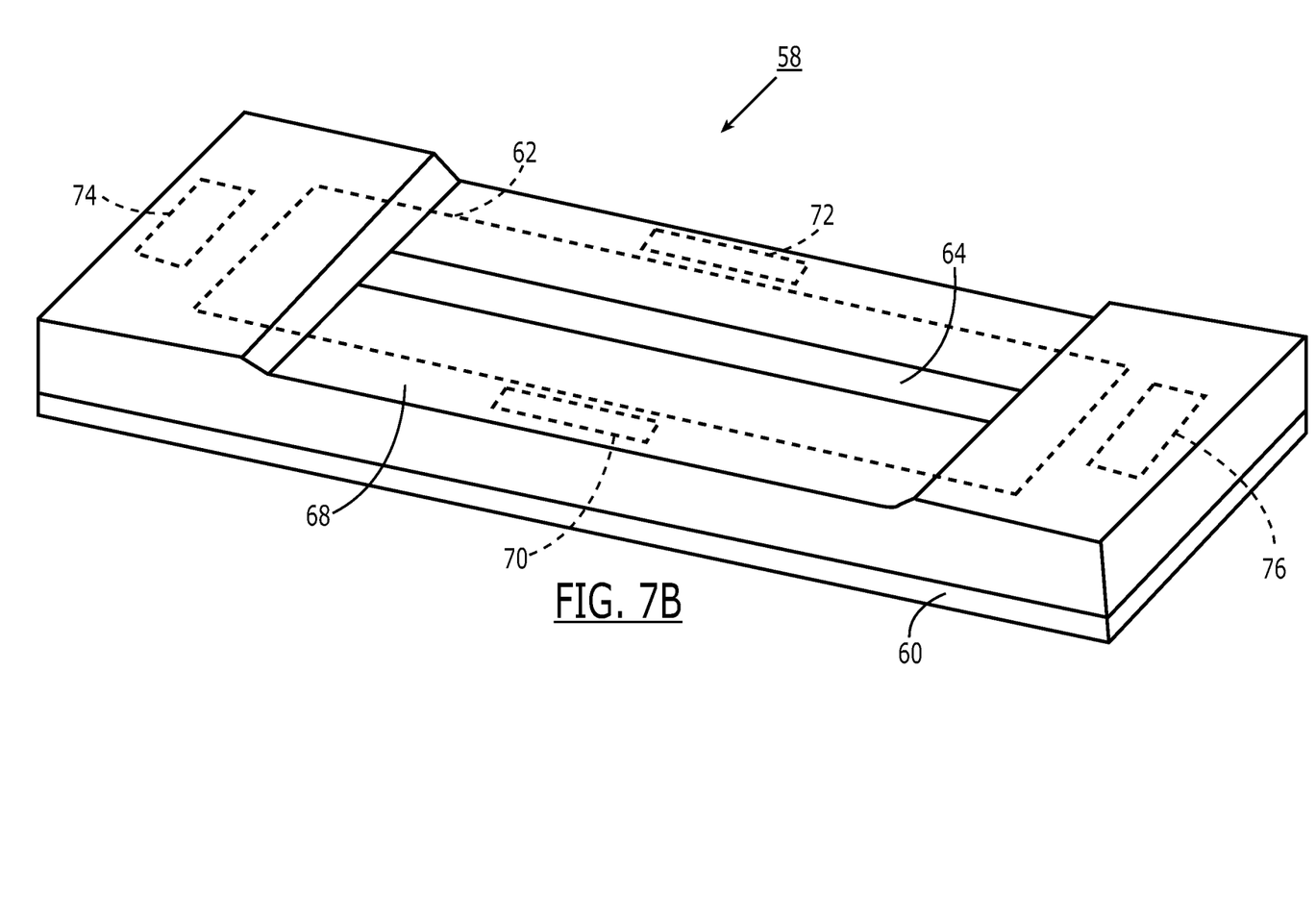
FIG. 7B is a perspective view of the integrated circuit (IC) package with multiple integrally encapsulated light sources and exposed IC surface of FIG. 7A, but with the light sources not illuminated, highlighting that the light sources cannot be seen through the encapsulation structure.

With reference to FIGS. 7A and 7B which are perspective views of the embodiment 58 of the present invention shown in FIGS. 4, 5, and 6, the "on" and "off"-states of light sources 70-76 are illustrated. In FIG. 7A, all light sources 70-76 are in an operating state (i.e., current is applied to the terminals thereof so as to cause the light sources to emit light). In this state, light emits at the surface of encapsulation structure 68, preferably such that the physical surface of the light sources are not visible through the encapsulation material. However, as illustrated in FIG. 7B, when light sources 70-76 are not in an operating state the physical surface of the light sources are not visible through the encapsulation material. Indeed, there is otherwise no clue that there are in fact light sources forming a part of the structure of embodiment 58, and the structure appears otherwise as a typical encapsulated capacitive fingerprint sensor structure, with all of the equivalent properties and characteristics of an encapsulating structure which does not contain a light source.

Figure 8:
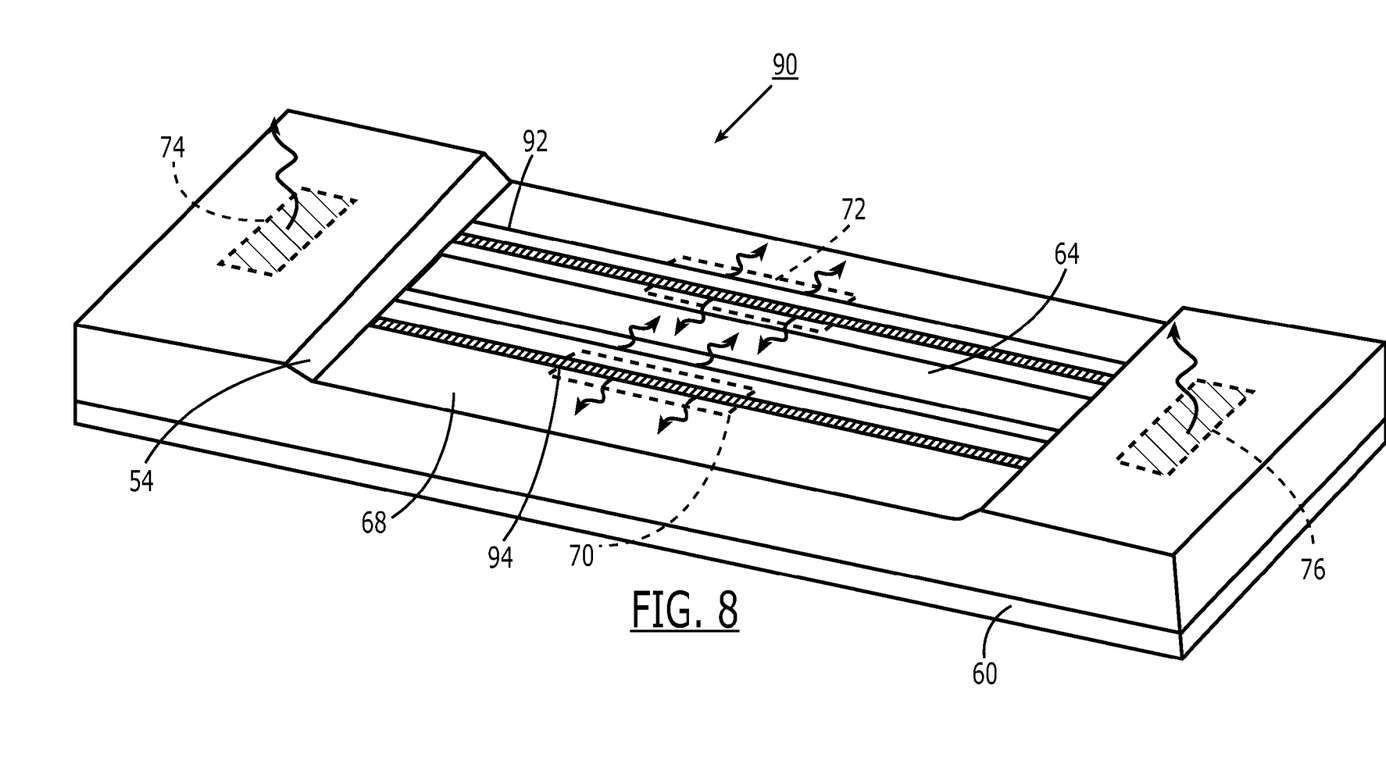
FIG. 8 is a perspective view of the integrated circuit (IC) package with multiple integrally encapsulated illuminated light sources and exposed IC surface which includes a plurality of bezels for making electrical connection to the finger being scanned, according to an embodiment of the present invention.

With reference next to FIG. 8, there is shown therein another embodiment 90 of the present invention. The elements of embodiment 90 are the same as those of embodiment 58, and hence the same reference numbers are used therein, with the exception of the addition of a bezel structure comprised of conductive bezel plates 92, 94. In certain embodiments of a fingerprint sensor it is desirable to make electrical connection between the finger being scanned and the sensor IC 64. One method of making this electrical connection to the finger is to provide proximate the sensor IC conductive bezels such as 92 and 94, which are formed of a conductive and environmentally robust material such as stainless steel. The material forming such bezels is often very opaque, with a density that permits little if any light from light sources 70, 72 to pass therethrough. However, with the proper choice of thicknesses, placement of light sources 70, 72, etc., light from light sources 70, 72 can exit under and around bezels 92, 94, as illustrated. Indeed, this may be viewed as an advantage in that by locating bezels 92, 94 at or near the surface of encapsulation structure 68, light may be directed by bezels 92, 94 to their edges axial to the direction of finger motion. This allows the desired visual feedback, aesthetic appearance, differentiation, etc. discussed above despite the presence of opaque bezels 92, 94.

Accordingly, the present invention uses traditional materials, tools, and processes to manufacture an IC packages with concealed light sources. Other than the cost of the LED(s) and the cost to mount them, there is no other additional cost of materials or manufacture as compared conventional IC packages. Additional yield losses and additional manufacturing steps and cycle time are both minimized.

While a plurality of preferred exemplary embodiments have been presented in the foregoing detailed description, it should be understood that a vast number of variations exist, and these preferred exemplary embodiments are merely representative examples, and are not intended to limit the scope, applicability or configuration of the disclosure in any way.

Figure 9:
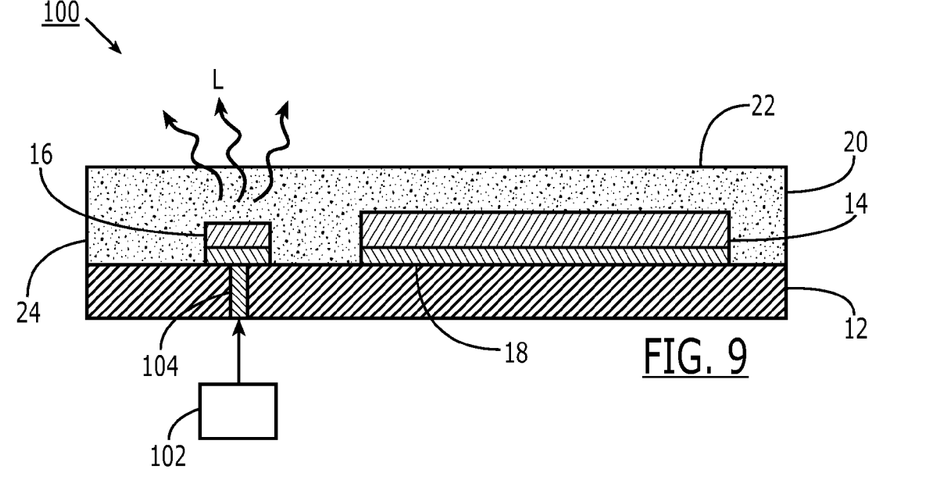
FIG. 9 is a cut-away cross-sectional view of an integrated circuit (IC) package with integrally encapsulated light source, where the light source is controlled by an external control element, according to an embodiment of the present invention.

Referring again to FIG. 1, light source 16 is shown in direct, electrical communication with IC 14. Accordingly, IC 14 can control the operation of light source 16. However, other embodiments for controlling the operation of light source 16 are within the scope of the present invention. One such embodiment 100 is illustrated in FIG. 9. According to this embodiment, IC 14 and light source 16 are not in direct electrical communication with one another. Rather, control element 102 (passive or active) communicates with light source 16 by means of conductive via 104 or other connection mechanism. According to this embodiment, control element 102 is shown separate from the integrated circuit package containing IC 14 and light source 16 within encapsulation structure 20. In this instance, control element 102 may be an element of a system into which embodiment 100 is ultimately installed, such as a personal computer, cellular telephone, PDA, etc. Control element 102 may alternatively be an element, discrete and separate from IC 14 and light source 16, contained within the integrated circuit package. In either case, IC 14 does not play a role in the control of light source 16, so that control of light source 16 is external to IC 14.

Figure 10:
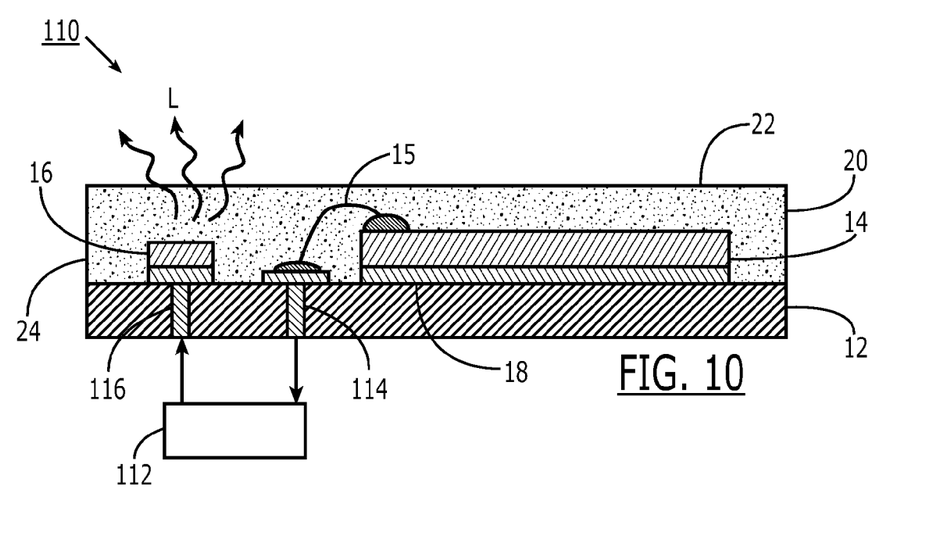
FIG. 10 is a cut-away cross-sectional view of an integrated circuit (IC) package with integrally encapsulated light source, where the light source is indirectly controlled by the integrated circuit via the external control element, according to an embodiment of the present invention.

In still another embodiment 110 of an integrated circuit package illustrated in FIG. 10, IC 14 and light source 16 are connected to control element 112 by means of vias 114, 116, respectively. Control element 112 is once again shown separate from the integrated circuit package, but may be a discrete, separate element therein in appropriate applications. According to embodiment 110, IC 14 is electrically coupled to and at least partially controlling control element 112, which in turn controls light source 16. In this way, IC 14 indirectly controls the operation of light source 16 via control element 112.

The present invention lends itself to many different applications. One exemplary embodiment described above is the exposed surface capacitive-type strip fingerprint sensor. However, this is simply one of many such applications. Other equally viable applications in the biometric sensor area include so-called area sensors (in which a finger is positioned in place over the sensor during scanning), non-capacitive sensors (e.g., thermal or optical sensors), retinal scan sensors, and so forth. Importantly, biometric sensing is just one area of application of the present invention. Any application in which visual cues, feedback, or aesthetics are desired while minimizing device size, cost, and departure from known materials and processes may benefit from the present invention. Accordingly, it is not practicable to list all possible applications herein. Thus, several embodiments are illustrated above, and one skilled in the art will appreciate other applications as appropriate.

Furthermore, various presently unforeseen or unanticipated alternatives, modifications variations, or improvements therein or thereon may be subsequently made by those skilled in the art which are also intended to be encompassed by the claims, below.

Therefore, the foregoing description provides those of ordinary skill in the art with a convenient guide for implementation of the disclosure, and contemplates that various changes in the functions and arrangements of the described embodiments may be made without departing from the spirit and scope of the disclosure defined by the claims thereto.

What is claimed is:

1. An integrated circuit package comprising:
an integrated circuit structure defining a biometric sensor;
a plurality of light sources positioned around a periphery of said biometric sensor; and
a semi-opaque encapsulation material, encapsulating at least a portion of said integrated circuit structure and said plurality of light sources such that said plurality of light sources and at least a portion of said integrated circuit structure are not visible to the unaided human eye, and configured so that light emitted from said plurality of light sources is visible to the unaided human eye through at least a portion of said semi-opaque encapsulation material to provide visual feedback to a user.

2. The integrated circuit package of claim 1, wherein said plurality of light sources are electrically coupled to said integrated circuit structure.

3. The integrated circuit package of claim 1, wherein said plurality of light sources are configured to be electrically coupled to and at least partially controlled by a device external to said integrated circuit package.

4. The integrated circuit package of claim 1, wherein said plurality of light sources and said integrated circuit structure are configured to be electrically coupled to a device external to said integrated circuit package.

5. The integrated circuit package of claim 1, wherein said plurality of light sources comprise at least one of a light emitting diode, an organic light emitting diode, and a solid state laser.

6. The integrated circuit package of claim 1, where said plurality of light sources form a part of said integrated circuit structure.

7. The integrated circuit package of claim 1, wherein at least two of said plurality of light sources each emit light of a different color such that said light so emitted is visible to the unaided human eye through at least a portion of said semi-opaque encapsulation material.

8. The integrated circuit package of claim 1, wherein said plurality of light sources are electrically connected to and controlled by circuitry for causing said light sources to emit light in patterns.

9. An integrated circuit package comprising:
an integrated circuit structure defining a fingerprint sensor;
a plurality of light sources positioned around a periphery of said fingerprint sensor;
a semi-opaque encapsulation material, encapsulating at least a portion of said integrated circuit structure and said plurality of light sources such that said plurality of light sources and at least a portion of said integrated circuit structure are not visible to the unaided human eye, and configured so that light emitted from said plurality of light sources is visible to the unaided human eye through at least a portion of said semi-opaque encapsulation material to provide visual feedback to a user.

10. The integrated circuit package of claim 9, wherein said plurality of light sources are electrically coupled to said integrated circuit structure.

11. The integrated circuit package of claim 9, wherein said plurality of light sources are configured to be electrically coupled to and at least partially controlled by a device external to said integrated circuit package.

12. The integrated circuit package of claim 11, wherein said plurality of light sources and said integrated circuit structure are configured to be electrically coupled to a device external to said integrated circuit package.

13. The integrated circuit package of claim 9, wherein said plurality of light sources comprise at least one of a light emitting diode, an organic light emitting diode, and a solid state laser.

14. The integrated circuit package of claim 9, where said plurality of light sources form a part of said integrated circuit structure.

15. The integrated circuit package of claim 9, wherein at least two of said plurality of light sources each emit light of a different color such that said light so emitted is visible to the unaided eye through at least a portion of said opaque encapsulation structure.

16. The integrated circuit package of claim 9, wherein said plurality of light sources are electrically connected to and controlled by circuitry for causing said light sources to emit light in patterns.

17. The integrated circuit package of claim 16, wherein said light sources emit light in patterns indicative of visual cues as to expected user action including at least one of an indication that the integrated circuit package is ready for presentation of a user's finger, a sensed fingerprint matches a stored fingerprint pattern, a user's finger was insufficiently or incorrectly presented, and a sensed fingerprint does not match a stored fingerprint pattern.

18. The integrated circuit package of claim 9, wherein said encapsulation material defines an exposed sensor region within which a portion of said fingerprint sensor is visible within said encapsulation material to the unaided human eye.

19. The integrated circuit package of claim 18, wherein said fingerprint sensor comprises a capacitive fingerprint sensor.

20. The integrated circuit package of claim 18, wherein the encapsulation material includes regions having thicknesses and geometries configured such that light emitted by said plurality of light sources and visible at a first region of said encapsulation material is of a different intensity than the light emitted by said plurality of light sources and visible at a second region of said encapsulation material.

21. The integrated circuit package of claim 18, wherein said exposed sensor region is defined by sidewalls extending downward from a top surface of said encapsulation material to a position proximate said fingerprint sensor, and further wherein at least one of said plurality of light sources is positioned relative to at least one of said sidewalls such that when said light source is caused to emit light, at least a portion of the light so emitted is visible to the unaided human eye through at least a portion of said at least one of said sidewalls, and still further wherein said light source is not visible to the unaided human eye through said sidewall.

22. The integrated circuit package of claim 21, wherein at least two of said light sources are each positioned relative to a corresponding one of said sidewalls such that when each said light source is caused to emit light, at least a portion of the light so emitted is visible to the unaided human eye through at least a portion of said sidewall corresponding to said light source, and still further wherein said light sources are not visible to the unaided human eye through said sidewalls.

* * * * *